United States Patent [19]

Hiyama et al.

[11] Patent Number: 5,361,203
[45] Date of Patent: Nov. 1, 1994

[54] ENDOSCOPE IMAGE DATA FILING SYSTEM AND AN ENDOSCOPE IMAGE DATA MANAGING METHOD FOR MANAGING A LARGE NUMBER OF IMAGE DATA IN VARIOUS MODE

[75] Inventors: Keiichi Hiyama; Masahide Kanno; Masakazu Nakamura; Kenichiro Nimoda, all of Tokyo, Japan

[73] Assignee: Olympus Optical Co., Ltd., Tokyo, Japan

[21] Appl. No.: 44,169

[22] Filed: Apr. 8, 1993

[30] Foreign Application Priority Data

Apr. 14, 1992 [JP] Japan .................................. 4-94461

[51] Int. Cl.$^5$ ............................................ G06F 15/00
[52] U.S. Cl. ............................................. 364/413.13
[58] Field of Search ................... 364/413.13; 128/4, 6; 358/98, 426, 448, 461, 403

[56] References Cited

U.S. PATENT DOCUMENTS 5,111,306  5/1992  Yamagami ........................ 358/426
5,216,518  6/1993  Kanno et al. ..................... 358/403

FOREIGN PATENT DOCUMENTS

63-153957  6/1988  Japan .
2-115981   4/1990  Japan .
3-293393  12/1991  Japan .
4-212336   8/1992  Japan .

Primary Examiner—Roy N. Envall, Jr.
Assistant Examiner—Khai Tran
Attorney, Agent, or Firm—Armstrong, Westerman, Hattori, McLeland & Naughton

[57] ABSTRACT

This invention provides an endoscope image data filing system comprising: a plurality of endoscope devices and a plurality of ultrasonic endoscope devices; an image data recording device which records a plurality of image information after reversibly and irreversibly compressing image signals received from the plurality of the endoscope devices and from the plurality of the ultrasonic endoscope devices; an image reproducing device (A) and an image reproducing device (B) for reproducing the image information recorded in the image data recording device; a large capacity data recording device which as required reads and writes the compressed image information recorded in the image data recording device; and a data communication device for performing communication between the image data recording device and an external host computer via a data input/output terminal device. In use of the endoscope image data filing system of the present invention, operators can manages the endoscope image data in various modes for a middle or long period. Thus, based on the patient history recorded in the endoscope image data filing system of the present invention, operators can make easily diagnosis on the patient.

13 Claims, 10 Drawing Sheets

| ID NO. HEADER | EXAMINATION ID |

FIG.7(b)

| ID NO. HEADER | PATIENT ID |

FIG.7(c)

| PATIENT'S NAME HEADER | PATIENT'S NAME |

ENDOSCOPE IMAGE DATA FILING SYSTEM AND AN ENDOSCOPE IMAGE DATA MANAGING METHOD FOR MANAGING A LARGE NUMBER OF IMAGE DATA IN VARIOUS MODE

BACKGROUND OF THE INVENTION

1. Field of the Invention

The present invention relates to an endoscope image data filing system and to an endoscope image data managing method for recording a large number of image data in a plurality of recording means and for managing these image data in various modes.

2. Description of the Related Art

In recent years, endoscopes have been widely used to observe a viscus in a coelom on a monitor display and thus to make examination or diagnosis by inserting an insertion unit of the endoscope into the coelom so as to form an image on an image-sensing means such as a solid-state image sensor.

In such an endoscope system, endoscope images obtained with an electronic endoscope unit are stored on a storage medium such as a magneto-optic disk in an image-data filing system so that these endoscope images can be effectively used for later diagnoses. It is required that the system for this purpose can be easily used.

In a first known system for such a purpose, disclosed in Japanese Patent Application Laid-Open No. 63-153957, an analog image data filing system is combined with a digital image data filing system. More important image data, for example, may be stored in the digital image data filing system and image data which have become less important may be stored in the analog image data filing system.

A second example of a known system is disclosed in Japanese Patent Application Laid-Open No. 2-115981, in which an analog image data filing system is combined with a digital image data filing system in such a way that either one of them can be selected to store the image data by performing selection on an endoscope unit.

In a third known system, disclosed in Japanese Patent Application Laid-Open No. 3-293393 or in Japanese Patent Application Laid-Open No. 4-212336, image data obtained in an endoscope examination room are stored in digital form on a magneto-optic disk, then the magneto-optic disk may be transferred to a distant conference room where the recorded image may be played back.

In the first and second known systems described above, a total system comprises an image input unit, a digital image data filing unit, an analog image data filing unit, and a filing controller for controlling these units. When another same type system is used at the same time, data communication between a plurality of the systems is needed. However, there is no description regarding the data management required for such data communication in the above corresponding patent applications.

In the case where a plurality of such systems are used, when previous endoscope image data are required as references for diagnosis it is impossible to make effective retrieval for endoscope image data, because image data are managed separately in each system and no unified management is done.

In the third known system, image data are recorded on a magneto-optic disk in an examination room, then the magneto-optic disk may be transferred to a distant room such as a conference room where the recorded image may be played back. However, there is no description reguarding the management of magneto-optic disks required when a lot of image data for a large number of examinations are recorded on a plurality of magneto-optic disks.

When endoscope image data are retrieved reguarding a certain patient, it is needed to set a magneto-optic disk one after another to an image-data filing system so as to check if the disk includes required image data, because there is no means to tell on which disk the required data are recorded.

In the prior art, as described above, when a plurality of recording media such as magneto-optic disks are used, the system is not easy to use, because unified management is not carried out on these plural recording media.

SUMMARY OF THE INVENTION

It is an object of the present invention to provide an endoscope image data filing system and a management method for endoscope image data, whereby the endoscope image data are compressed by means of plural methods and recorded on a plurality of recording means so that unified management can be performed on these endoscope image data.

In accordance with the present invention, an endoscope-image data filing system comprises: a plurality of endoscope devices for observing the inside of a coelom; a compression means including at least two methods for compressing an endoscope image signal received from the plurality of the endoscope devices; a first recording means for recording compressed image information obtained by the compression means; and a second recording means for recording compressed image information obtained by at least one method of the compression means.

Other features and advantages of the present invention will become apparent from the following description.

BRIEF DESCRIPTION OF THE DRAWINGS

FIGS. 1–14 are concerned with an embodiment in accordance with the present invention, wherein:

DETAILED DESCRIPTION OF THE PREFERRED EMBODIMENTS

Figure 1:
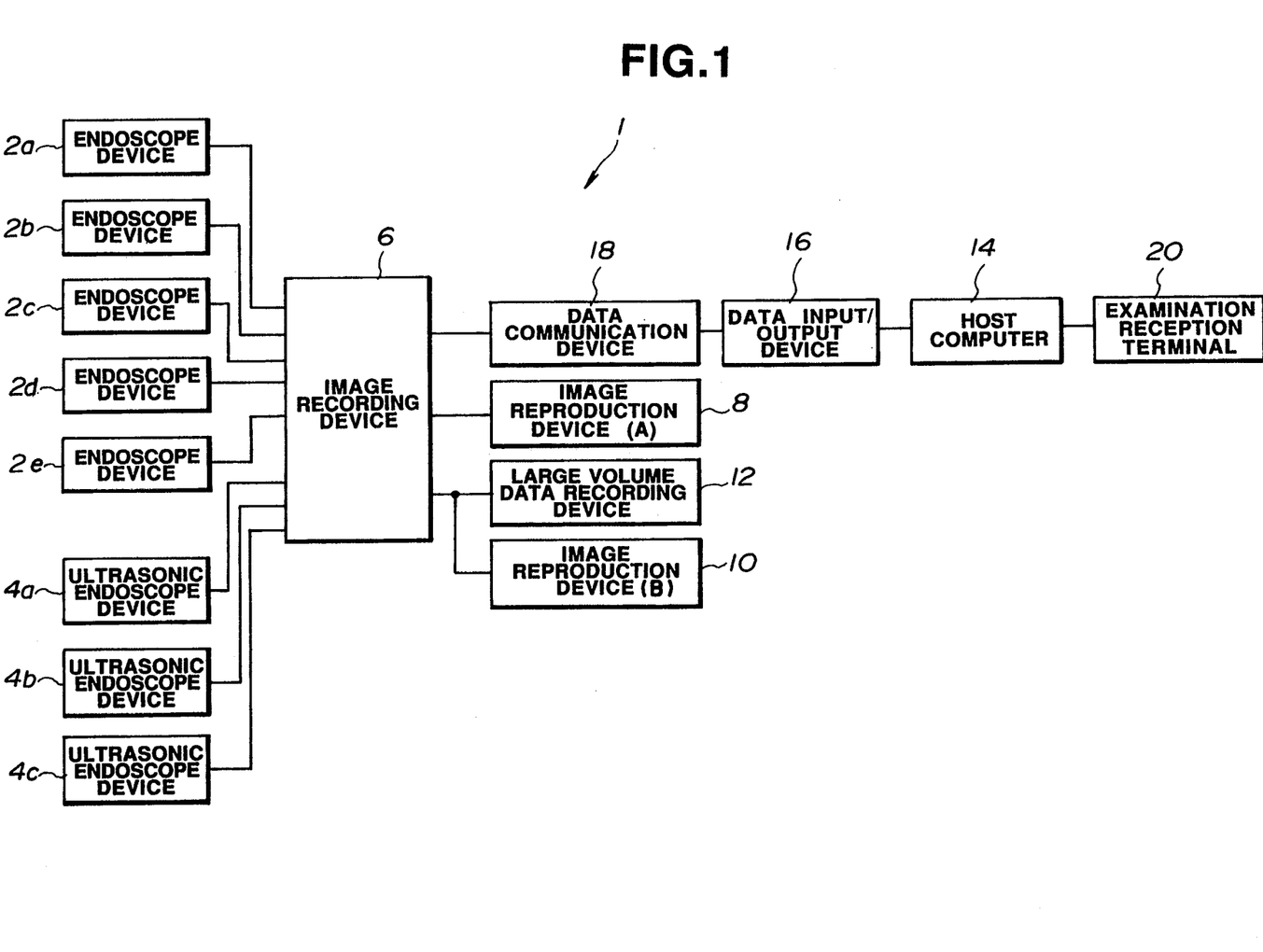
FIG. 1 is a block diagram showing the configuration of an endoscope image data filing system.

As shown in FIG. 1, an embodiment of an endoscope image data filing system in accordance with the present invention comprises: a plurality, for example, five (5), of endoscope devices 2a–2e which are to be inserted in a coelom so as to observe and treat a target portion, the endoscope devices being disposed in an examination room such as a satellite room; a plurality, for example, three (3), of ultrasonic endoscope devices 4a–4c which are to be inserted in a coelom so as to obtain ultrasonic images; an image recording device 6 for performing reversible and irreversible compression processing on image signals received from five endoscope devices 2a–2e and three ultrasonic endoscope devices 4a–4c and for further recording these compressed image signals as a plurality of pieces of image information, the image recording device 6 being disposed in, for example, an intensive care room; an image reproduction device (A) 8 and an image reproduction device (B) 10 disposed in, for example, a conference room for playing back the image information recorded in the image recording device 6; a large volume data recording device 12 for timely reading out and storing irreversibly-compressed image information recorded in the image recording device 6; and data communication device 18 for performing communication between the image recording device 6 and an external host computer 14 via a data input/output device 16. Data with respect to a patient to be examined with the endoscope devices 2a–2e or ultrasonic endoscope devices 4a–4c are input to the host computer 14 via an examination reception terminal connected to the host computer 14, and the input data are sent to the image recording device 6 via the data communication device 18 so that these input data are stored in a database.

Figures 2A, 2B:
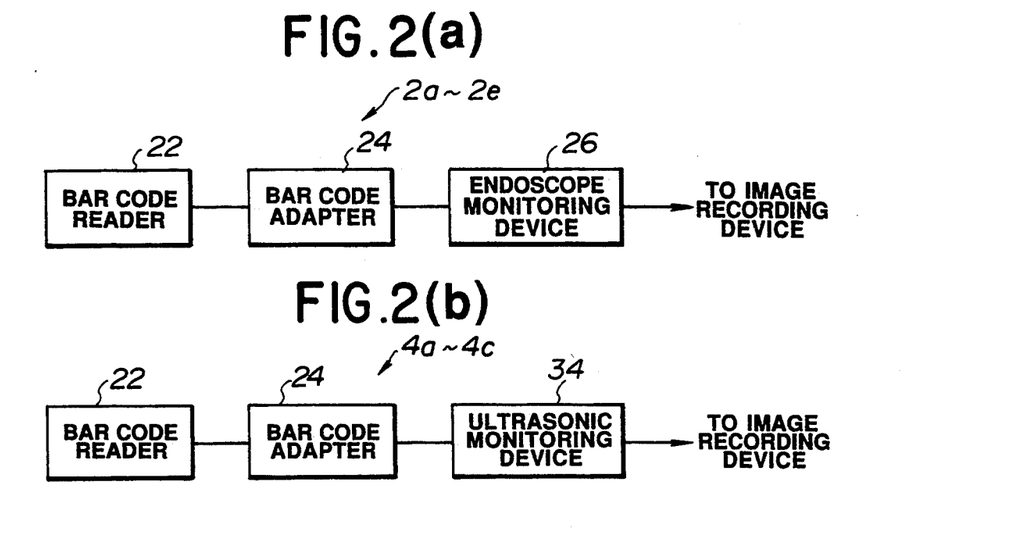
FIGS. 2(a) and 2(b) are a block diagram showing the configurations of an endoscope device and an ultrasonic endoscope device.

Each of the endoscope devices 2a–2e, as shown in FIG. 2(a), comprises: a bar code reader 22 for reading patient's ID or examination ID represented with bar codes; a bar code adapter 24 for converting the patient's ID data or examination ID data read with the bar code reader 22 into a predetermined communication format such as a RS-232C format; and an endoscope monitoring device 26 for retrieving data of the patient on the basis of the patient's ID data or examination ID data being input via the bar code adapter 24, and for also performing endoscopic observation.

Figure 3:
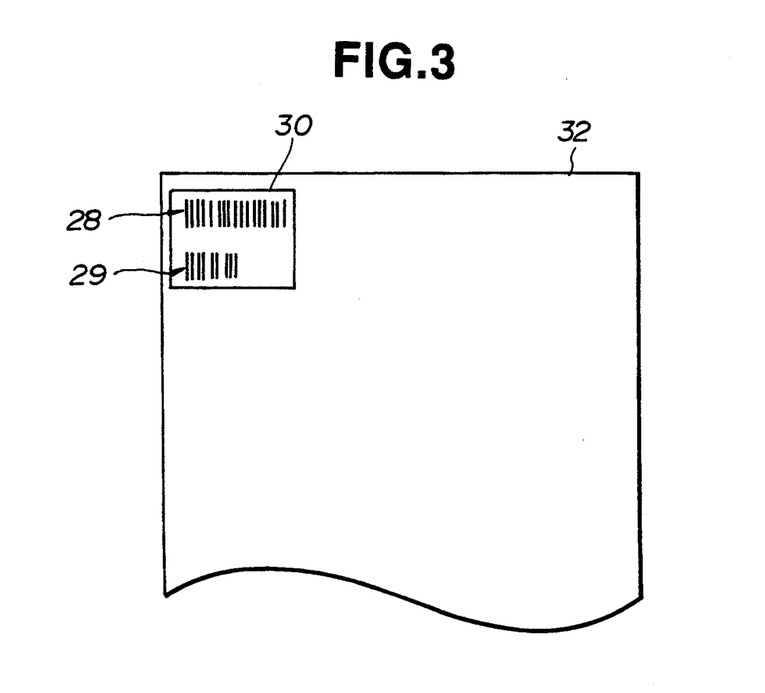
FIG. 3 is a schematic description for explanation of bar codes recorded on a patient card.

A patient's ID bar code 28 and an examination ID bar code 29 which are to be read with the bar code reader 22 are printed on a bar code sheet 30, then this bar code sheet 30 is stuck on a patient card 32 at a predetermined position, as shown in FIG. 3.

As shown in FIG. 2(b), each of the ultrasonic endoscope devices 4a–4c, like the endoscope devices 2a–2e, also comprises a bar code reader 22 of the same type as that in the endoscope devices 2a–2e; a bar code adapter 24 of the same type as that in the endoscope device 2a–2e; and an ultrasonic endoscope monitoring device 34 for retrieving data of the patient on the basis of the patient's ID data or examination ID data being input via the bar code adapter 24, and for also obtaining an ultrasonic endoscope image.

Figure 4:
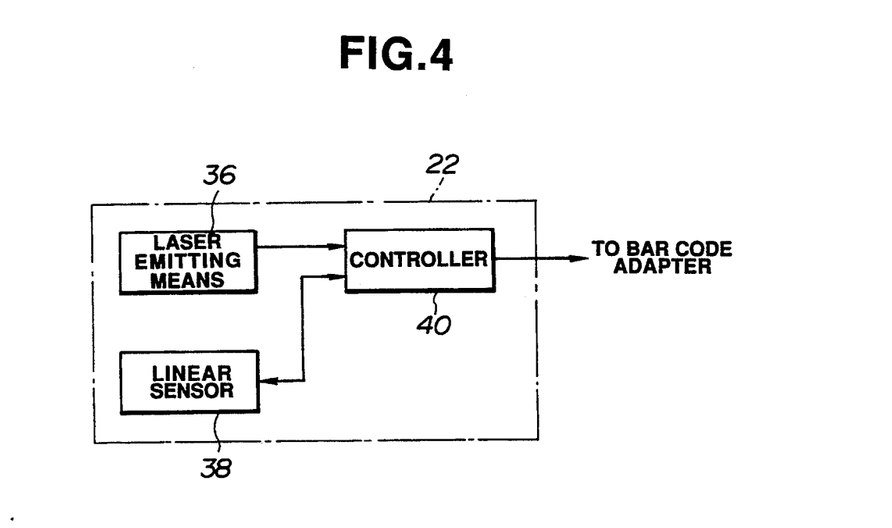
FIG. 4 is a block diagram showing the configuration of a bar code reader.

As shown in FIG. 4, the bar code reader 22 comprises: a laser emitting means 36 for illuminating the patient's ID bar code 28 or the examination ID bar code 29 with laser light; a one-dimensional sensor 38 for detecting one-dimensional information from the light reflected from the patient's ID bar code 28 or the examination ID bar code 29; and a controller 40 for controlling the operation of the laser emitting means 36 and the operation of the one-dimensional sensor 38 and for further transmitting the one-dimensional information detected with the one-dimensional sensor 38 as patient's ID or examination ID to the bar code adapter 24.

Figure 5:
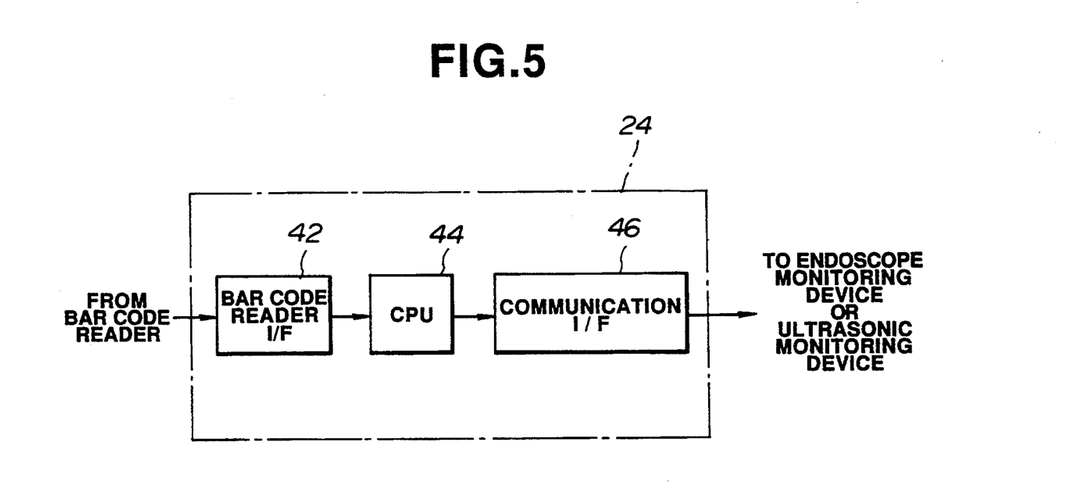
FIG. 5 is a block diagram showing the configuration of a bar code adapter.

The bar code adapter 24, as shown in FIG. 5, comprises: a bar code reader interface 42 for inputting the patient's ID data or the examination ID data transmitted from the controller 40; a CPU 44 for converting the patient's ID data or the examination ID data being input into data in a predetermined communication format; and a communication interface 46 whereby communication is carried out with the endoscope monitoring device 26 or the ultrasonic endoscope monitoring device 34.

Figure 6:
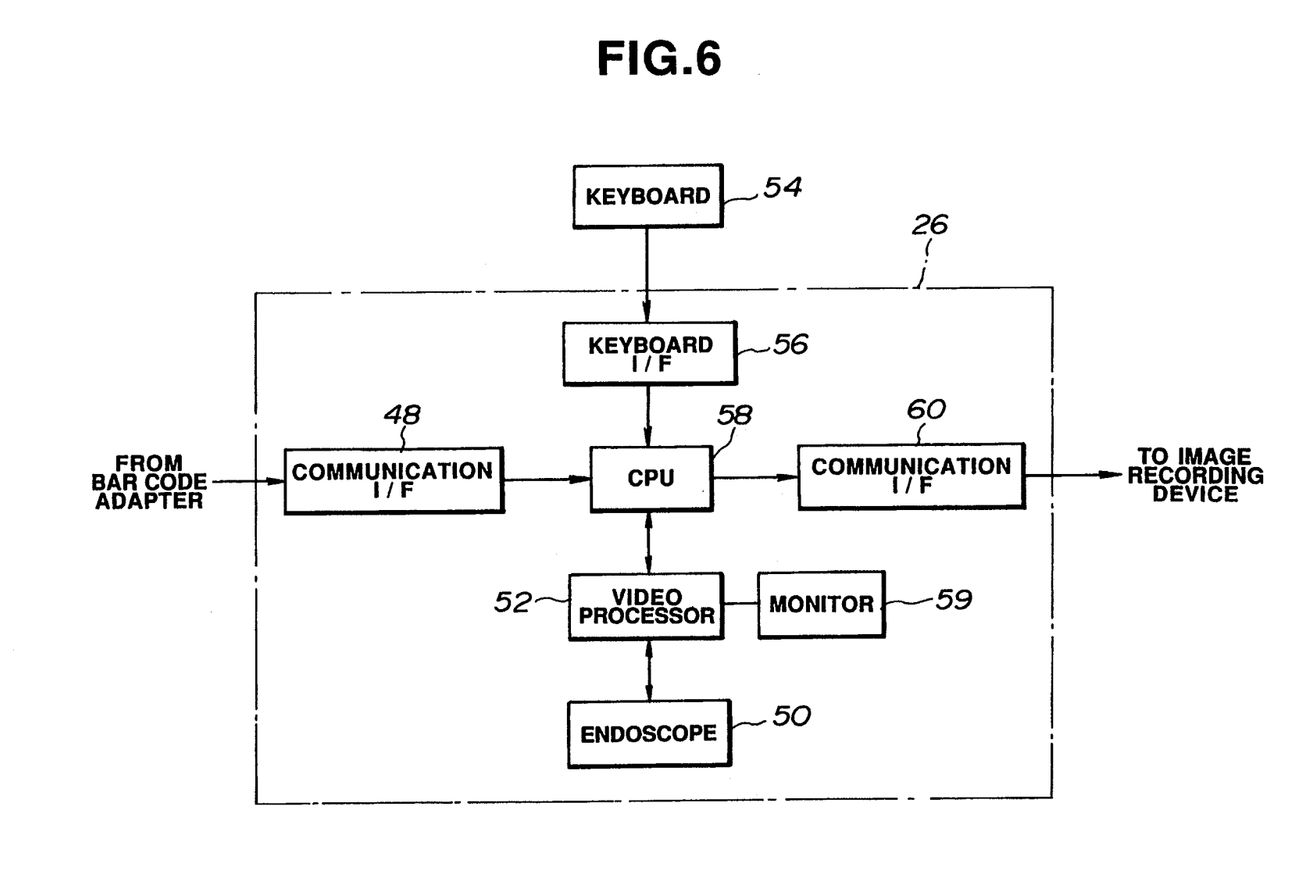
FIG. 6 is a block diagram showing the configuration of an endoscope monitoring device.

As shown in FIG. 6, the endoscope monitoring device 26 comprises: a communication interface 48 for performing communication with the communication interface 46 of the bar code adapter 24; an endoscope 50 to be inserted into a coelom so as to obtain an image of a portion to be observed; a video processor 52 for producing an endoscope image signal based on the signal received from the endoscope 50; a keyboard interface 56 for inputting data such as a patient's name and for inputting control commands via an external input means such as a keyboard 54; a CPU 58 for controlling the video processor 52 and for inputting data and commands via the communication interface 48 and via the keyboard interface 56; and a monitor display 59 for displaying the endoscopic image obtained with the endoscope or for displaying information recorded in the image recording device 6.

Figure 7A:
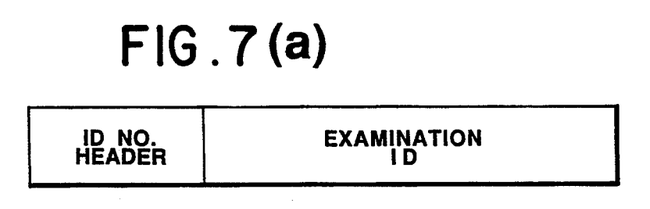
FIGS. 7(a), 7(b) and 7(c) are schematic descriptions for explanation of the data formats on an examination ID, a patient ID, and a patient's name, respectively.
Figure 7B:
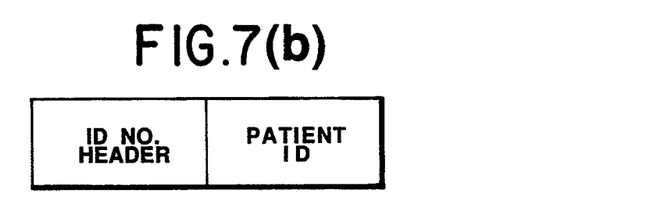
Figure 7C:
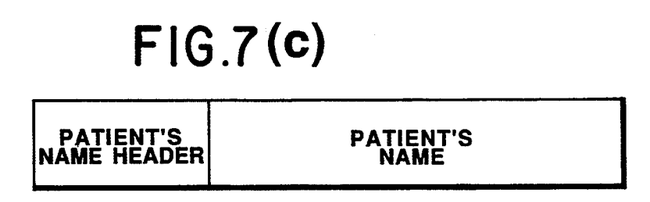

In accordance with the number of digits (for example, the patient's ID data consists of 8 digits and the examination ID data consists of 16 digits) of the patient's ID data or the examination ID data received via the communication interface 48, the CPU 58 adds an ID-number header indicating the type of the ID data at the head of the data as shown in FIGS. 7(a) and 7(b). When patient name data is input via the keyboard 54, the CPU 58 adds a patient name header on the head of the data. These data added with ID number header or patient name header, the endoscope image signal received from the video processor 52, and the control commands are transmitted to the image recording device 6 via the communication interface 60 (See FIG. 6).

The ultrasonic endoscope monitoring device 34 has a configuration similar to that of the endoscope monitoring device 26 with a difference that an ultrasonic endoscope (not shown) is used instead of the endoscope 50 to be inserted so as to obtain an ultrasonic image signal which is to be transmitted to the image recording device 6.

Figure 8:
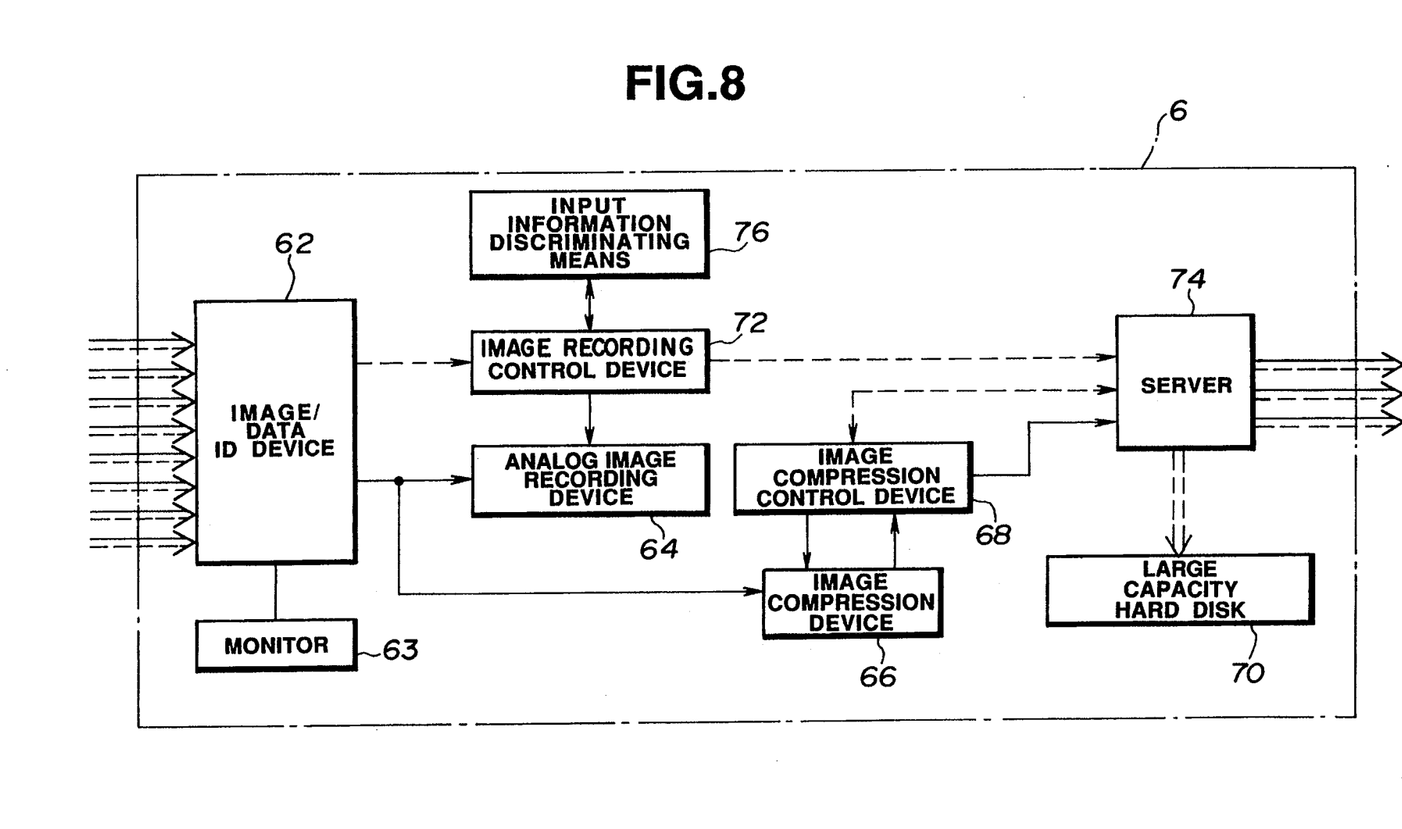
FIG. 8 is a block diagram showing the configuration of an image recording device.

As shown in FIG. 8, the image recording device 6 has an image/data input/output device 62 which inputs: the endoscope image signal or the ultrasonic image signal from the endoscope devices 2a–2e and from the ultrasonic endoscope devices 4a–4c; control commands; the patient's ID data or the examination ID data with the ID number header; and the patient's name data with the patient's name header; and which also outputs: the image data recorded in the image recording device 6 or in the large volume data recording device 12; and the patient data from the host computer 14, to the endoscope monitoring device 26 or to the ultrasonic endoscope monitoring device 34. The image/data input/output device 62 is connected to a monitor display 63 for displaying the images or the data which are input or output.

The image recording device 6 also includes: an analog image recording device 64 for recording the analog data of the endoscope image and the ultrasonic endoscope image together with the patient data via the image/data input/output device 62; an image compression device 66 for performing A/D conversion on the endoscope image and on the ultrasonic endoscope image so as to produce digital image data and for further performing at least two types of image data compression including reversible compression and irreversible compression on the digital image data; an image compression control device 68 for controlling the image compression device 66 and for adding the patient data to the compressed image data; a large capacity hard disk 70 for storing, for example, one-week reversibly-compressed image data and two-week irreversibly-compressed image data compressed by the image compression control device 68 in a patient examination database; and an image recording control device 72 for controlling the large capacity hard disk 70, the analog image recording device 64, and the image compression control device 68.

The image recording control device 72 controls the image compression control device 68 and the large capacity hard disk 70 via a server 74. The server 74 transmits the compressed image data from the image compression control device 68 to the large capacity hard disk 70 and also transmits the non-compressed digital image data, the compressed image data, and the control signals to the image reproduction device (A) 8, the image reproduction device (B) 10, and the large volume data recording device 12. The communication with the host computer 14 is also performed via the server 74. The image recording control device 72 is connected to an input information discriminating means 76 for determining which type of data, patient ID data, examination ID data, or patient name data, is input via the bar code reader 22 or via the keyboard 54. Based on the data type, patient ID data, examination ID data, or patient name data, being indicated by the input information discriminating means 76, the image recording control device 72 retrieves a patient data in the patient examination database stored in the large capacity hard disk 70 and transmits the obtained corresponding patient data to the endoscope devices 2a–2e or the ultrasonic endoscope devices 4a–4c.

The image recording control device 72 performs management individually for the patient data sent from the host computer 14 and image data sent from the endoscope devices 2a–2e or the ultrasonic endoscope devices 4a–4c. The image recording control device 72 records the image data sent from the endoscope devices 2a–2e or the ultrasonic endoscope devices 4a–4c on the large capacity hard disk 70 in the order of the time that the data is generated, and also records management data related to the image data in the database so that these recorded image data can be retrieved. The image recording control device 72 performs recording management in such a manner that when either one of the analog image recording device 64 or the large capacity hard disk 70 fails, the image data are recorded on the other one. The image recording control device 72 also performs management for a digital storage device (not shown) to make digital back-up copies of the input image signals.

Figure 9:
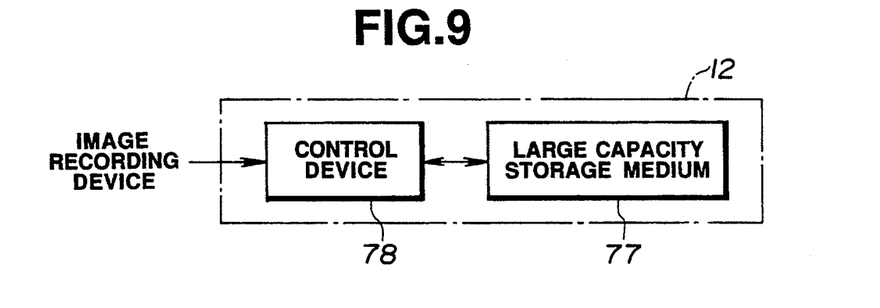
FIG. 9 is a block diagram showing the configuration of a large volume data recording device.

As shown in FIG. 9, the large volume data recording device 12 comprises: a large capacity storage medium 77 having such a capacity to store, for example, two-year irreversibly-compressed image data sent from the image recording control device 72; and a control device 78 for making communication with the image recording control device 72 so as to timely read the irreversibly-compressed image data from the large capacity hard disk 70 via the server 74 and for further recording the received irreversibly-compressed image data on the large capacity storage medium 77. When the remaining capacity of the large capacity storage medium 77 available for additional new image data becomes less than a predetermined amount, the control device 78 sends an alarm signal to the endoscope devices 2a–2e and the ultrasonic endoscope devices 4a–4c. In this situation, by pressing a key (not shown) on the control device 78, the large capacity storage medium 77 can be exchanged with a new one. The control device 78 has a database including the management data with respect to the non-compressed image data stored on the large capacity storage medium 77 so that these image data can be retrieved.

Figure 10:
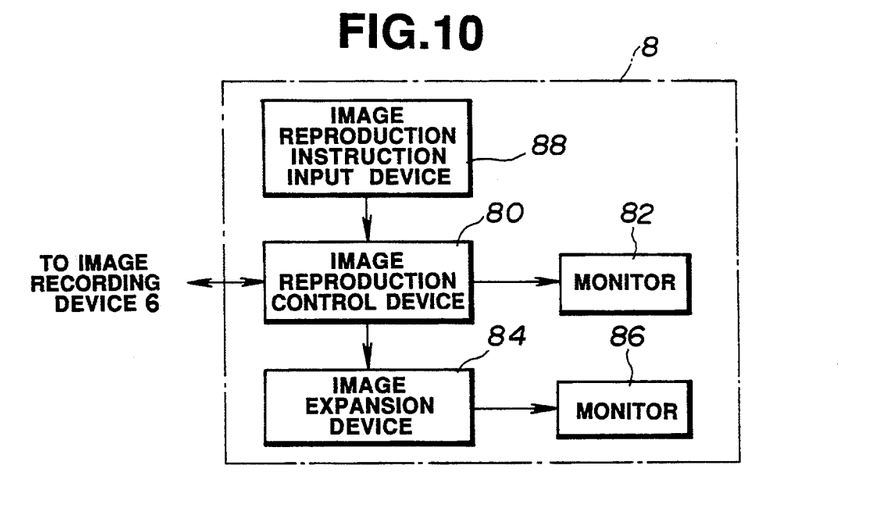
FIG. 10 is a block diagram showing the configuration of an image reproduction device (A)

As shown in FIG. 10, the image reproduction device (A) 8 comprises: an image reproduction control device 80 for receiving non-compressed digital image data, the reversibly-compressed image data, and the irreversibly-compressed image data, from the image recording device 6, and for further converting the non-compressed digital image data into an image signal in the format of, for example, NTSC; a monitor display 82 for displaying the non-compressed digital image; an image expansion device 84 for expanding the reversibly-compressed image data and the irreversibly-compressed image data; a monitor display 86 for displaying the image expanded by the image expansion device 84; and an image reproduction instruction input device 88 for giving instructions of image reproduction to the image reproduction control device 80; wherein based on the instruction from the image reproduction instruction input device 88, the image reproduction control device 80 reads image data to be expanded from the image recording device 6 and further displays these image data on the monitor display 86.

Figure 11:
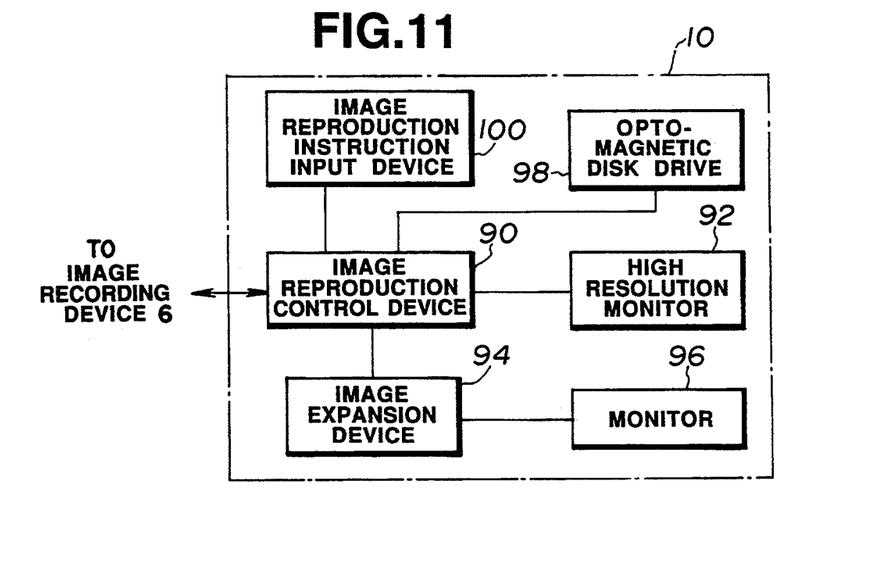
FIG. 11 is a block diagram showing the configuration of an image reproduction device (B)

As shown in FIG. 11, the image reproduction device (B) 10 comprises: an image reproduction control device 90 for receiving non-compressed digital image data, the reversibly-compressed image data, and the irreversibly-compressed image data, from the image recording device 6, and for further converting the non-compressed digital image data into, for example, a high-resolution image signal; a high-resolution monitor display 92 for displaying the non-compressed digital image; an image expansion device 94 for expanding the reversibly-compressed image data and the irreversibly-compressed image data; a monitor display 96 for displaying the image expanded by the image expansion device 94; a magneto-optic disk drive 98 connected to the image reproduction control device 90 for storing non-compressed digital image data, the reversibly-compressed image data, and the irreversibly-compressed image data; and an image reproduction instruction input device 100 for giving instructions of image reproduction to the image reproduction control device 90; wherein based on the instruction from the image reproduction instruction input device 100, the image reproduction control device 90 reads image data to be expanded from the image recording device 6 and further displays these image data on the monitor display 96.

Figure 12:
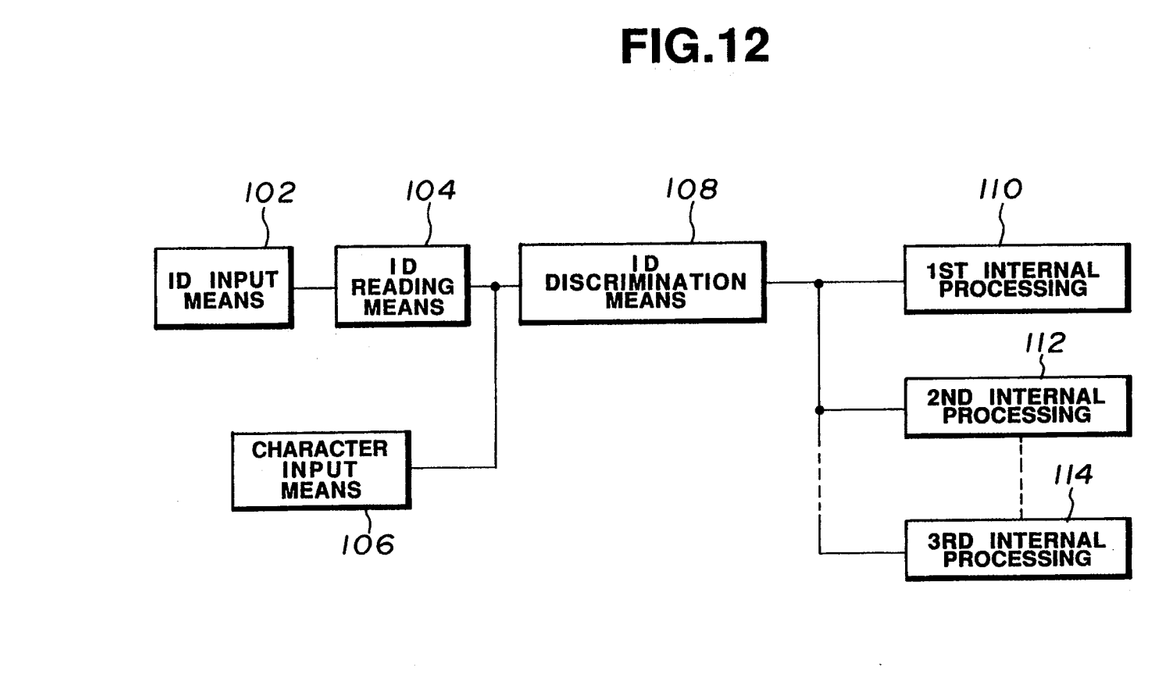
FIG. 12 is a schematic description showing the process for inputting examination information and patient information.
Figure 13:
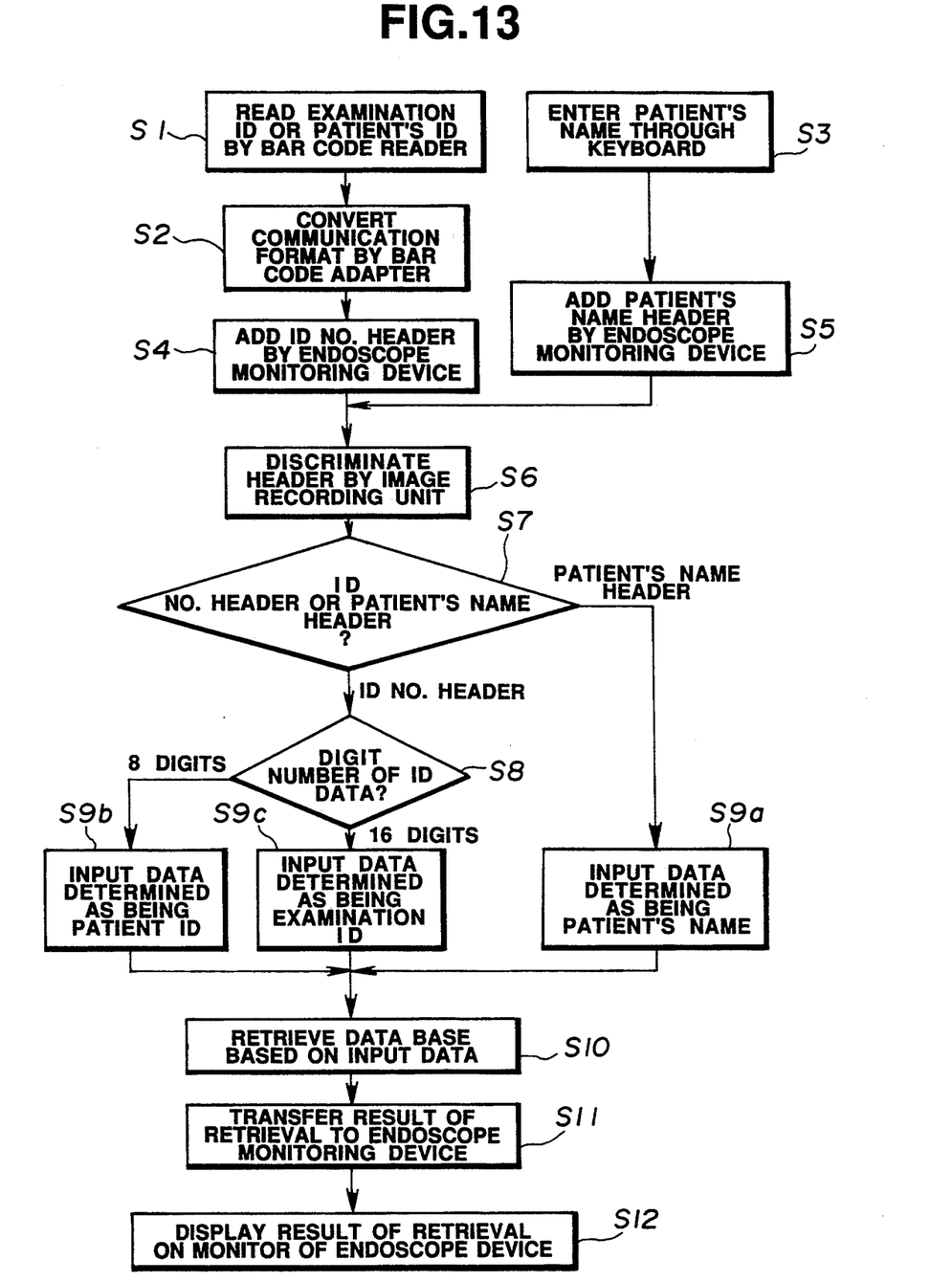
FIG. 13 is a flowchart showing the processing flow of inputting examination information and patient information.

The endoscopic image data filing system having such a configuration described above operates as follows:

As shown in FIG. 12, at the first step to start an endoscopic examination, an operator obtains patient's ID data or examination ID data by reading an ID input means 102 such as patient's ID bar code 28 and the examination ID bar code 29 provided on a patient card via an ID reading means 104 such as a bar code reader 22. When there is found neither patient's ID bar code 28 nor examination ID bar code 29 on the patient card because the patient is an emergency case, the patient's name is input via a character input means 106 such as a keyboard 54, then a ID number header and a patient's name header are added to the patient's ID data, the examination ID data, and the patient's name data via the endoscope monitoring device 26. An ID discrimination means 108 or the input information discriminating means 76 of the image recording device 6 determines which data type of patient's ID data, the examination ID data, and the patient's name data, the input data is. Then, depending on the data type of the input data, the image recording device 6 performs a first internal processing 110 (processing based on the patient's ID data), a second internal processing 112 (processing based on the examination ID data), or a third internal processing 114 (processing based on the patient's name data). Referring to FIG. 13, the processing described above will be explained in more detail. Examination with the endoscope device is started with a starting procedure. At step 1 (S1) of the first step of the starting procedure, the patient's ID bar code 28 or the examination ID bar code 29 is read by the bar code reader 22. In step S2, the format of the data is converted into a communication format by the bar code adapter 24, then the data is sent to endoscope monitoring device 26 or the like. In step S3, a patient name is input via the keyboard 54 and sent to the endoscope monitoring device 26 or the like. In steps S4 and S5, the endoscope monitoring device 26 adds an ID number header and a patient's name header to the patient's ID data, the examination ID data, and the patient's name data, then sends these data to the image recording device 6. In step S6, the input information discriminating means 76 of the image recording device 6 discriminates the ID number header and the patient's name header. In step S7, if the discrimination gives the conclusion that the data has an ID number header, then process proceeds to step S8. If the data has a patient's name header, then process proceeds to step S9a. Furthermore, in step S8, the input information discriminating means 76 determines the number of digits of the ID data from the ID number header. If the number of digits of the ID data is eight, then the process proceeds to step S9b. If the number of digits is 16, then the process proceeds to step S9c. In steps S9a–S9c, determination is carried out which one of patient's ID data, examination ID data, and patient's name data the input data is. Then, process proceeds to step S10, where based on the input data, the patient-data database in the large capacity hard disk 70 is retrieved for the patient data. In step S11, the result of the retrieval is sent to the endoscope monitoring device 26. In step S12, the result of the retrieval is displayed on the monitor display 59 of the endoscope monitoring device 26 or the ultrasonic endoscope monitoring device 34. Thus, the starting procedure is completed.

Figure 14:
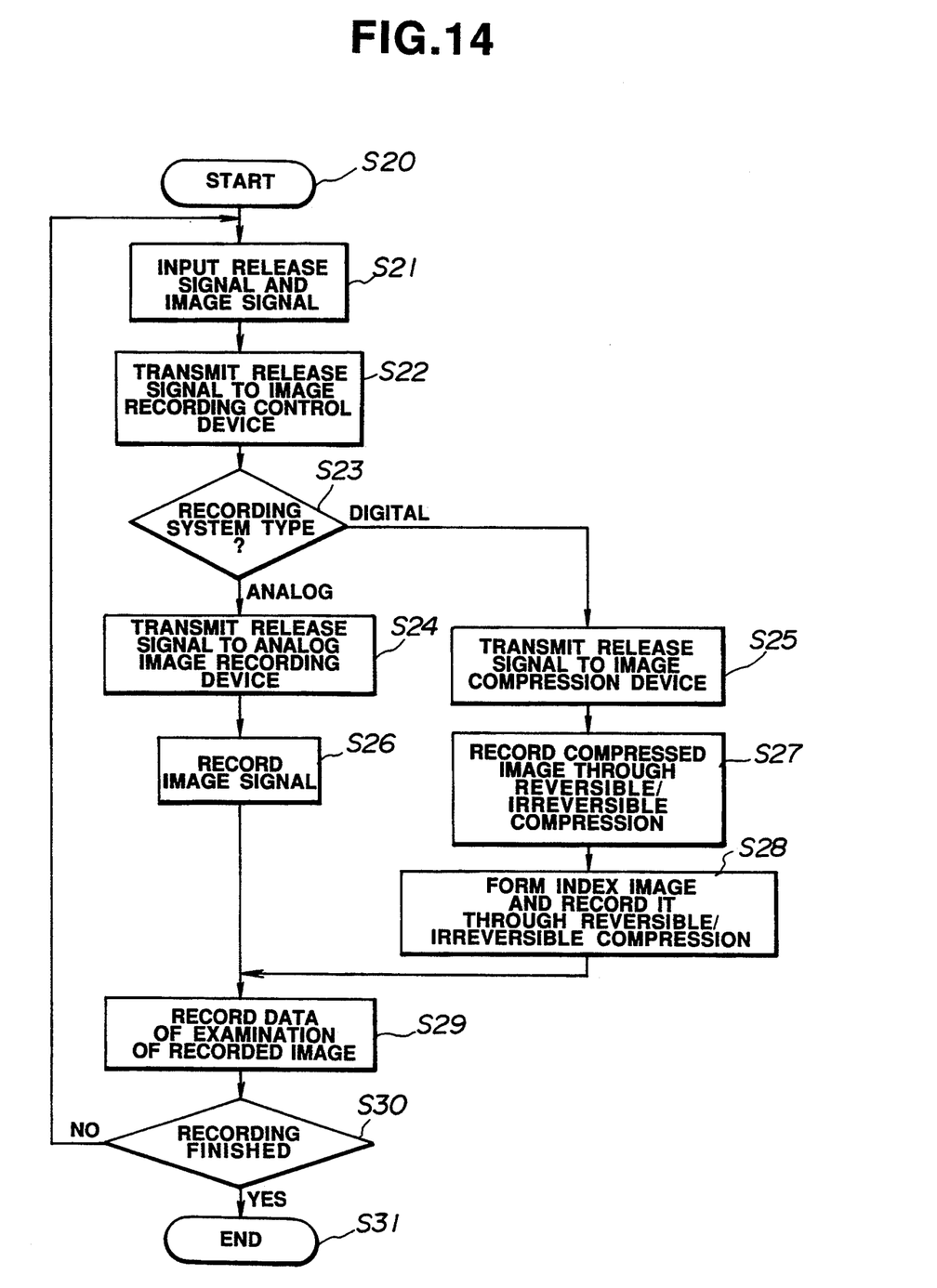
FIG. 14 is a flowchart showing the flow of data filing process carried out in an endoscope image data filing system.

After the starting procedure is completed as described above, an endoscope 50, for example, of the endoscope monitoring device 26, is inserted into a coelom to begin actual examination. When the operator finds out the desired portion to be examined with the endoscope, he/she begins recording the image data in step S20 as shown in FIG. 14. In step S21, a release signal indicating a recording mode and other information is input via the keyboard 54, then this input release signal and the endoscope image signal are sent to the CPU 58. In step S22, via the communication interface 60, the release signal and the endoscope image signal are applied to the image recording control device 72 of the image recording device 6, where the endoscope image signal is converted from the analog to digital form then stored in a memory (not shown). In step S23, the image recording control device 72 determines the recording mode. If the recording mode is an analog one, then the process proceeds to step S24. In the case of the digital recording mode, the process proceeds to step S25.

In step S24, the release signal and the endoscope image signal are applied to the analog image recording device 64, then in step S26, the endoscope image signal is recorded in the analog image recording device 64. After that, the process proceeds to step S29. In the case of the digital recording mode, the release signal is applied to the image compression control device 68 via the server 74, in step S25. Then in step S27, the endoscope image signal is applied to image compression device 66 where the endoscope image signal is converted from an analog signal to a digital signal. Furthermore, the image compression control device 68 controls the image compression device 66 to make reversible and irreversible compression on the endoscope image signal. Two types of compressed image data, that is, the reversibly-compressed and irreversibly-compressed image data, are stored on the large capacity hard disk via the server 74. At the same time, in step S28, index image data is produced and reversibly and irreversibly compressed. Then, the compressed index data are stored on the large capacity hard disk via the server 74. In the following step S29, the examination data related to the recorded image data, the track number of the analog image recording device on which the corresponding analog image data is recorded, and file name having the digital image data are added to the patient-data database in the large capacity hard disk 70. In step S30, it is determined if the recording process is completed. If the recording process is not completed yet, the process goes back to step S21 so as to repeat the steps until it is determined that the process is completed in step S30. If step 30 concludes that the process is completed, then the process ends in step S31.

As described above, two types of compressed image data, that is, the reversibly-compressed and irreversibly-compressed image data, are recorded on the large capacity hard disk 70, and the endoscope image signal is recorded in the analog image recording device 64. After the examination is finished, these image data together with the patient data and the examination data are played back on the image reproduction device (A) 8 and the image reproduction device (B) 10 so as to make detailed observation for diagnosis. The irreversibly-compressed image data stored on the large capacity hard disk 70 are transferred in a timely manner, for example, at night, when no examination is carried out, to the large volume data recording device 12 so as to make long-period storage. As required, these irreversibly-compressed image data together with the patient data and examination data are played back on the image reproduction device (A) 8 and the image reproduction device (B) 10.

In the above specific embodiment, the image data is recorded selectively either in analog form or in digital form. However, the image data may be recorded both in analog and digital forms at the same time.

The communication between the image recording device and the endoscope devices and also between the host computer and the image recording device may be carried out by communication means with optical isolators.

Depending on the experience level of the operators (doctor, student, etc.) each operator may be given his own password for use of the endoscope image data filing system 1 so that more adequate management can be performed with respect to the patient data.

As described above, in an embodiment of an endoscope image data filing system 1 in accordance with the present invention, endoscope image signals and ultrasonic endoscope image signals from endoscope devices 2a-2e and ultrasonic endoscope devices 4a-4c are recorded in analog form at a proper time. These image signals are further reversibly compressed and irreversibly compressed and recorded on a large capacity hard disk 70. Furthermore, the irreversibly-compressed image data stored on the large capacity hard disk 70 are transferred to a large volume data recording device 12 so as to make long-period storage. Two types of compressed image data, that is, the reversibly-compressed image data and the irreversibly-compressed image data recorded on the large capacity hard disk 70, and the irreversibly-compressed image data recorded on the large volume data recording device 12 for long-period storage, together with the patient data and the examination data can be played back as required on the image reproduction device (A) 8 and the image reproduction device (B) 10. Thus, operators can manage the endoscope image data in various modes for a middle or long period. Thus, based on the patient history recorded in such a manner described above, operators can make easily diagnosis on the patient.

It is evident that there may be a number of changes and modifications without departing from the spirit and scope of the invention. The present invention is not limited to the embodiments described herein but is only limited by the claims appended hereto.

What is claimed is:

1. An endoscope image data filing system comprising:
   a plurality of endoscope devices for observing the inside of a coelom;
   a compression means for compressing endoscope image signals received from said plurality of said endoscope devices by at least one reversible compression method for reversibly compressing said endoscope image signals and at least one irreversible compression method for irreversibly compressing said endoscope image signals;
   a first recording means for recording compressed image information produced in said compression means by both said reversible compression method and said irreversible compression method; and
   a second recording means for re-recording compressed image information recorded by said first recording means, said compressed image information produced by said irreversible compression method of said compression means.

2. An endoscope image data filing system as defined in claim 1 wherein said plurality of said endoscope devices include a plurality of optical endoscope devices for observing the inside of a coelom by means of optical images.

3. An endoscope image data filing system as defined in any of claims 1 and 4, wherein said plurality of said endoscope devices include a plurality of ultrasonic endoscope devices for observing the inside of a coelom by means of ultrasonic images.

4. An endoscope image data filing system as defined in any of claims 1, 2, and 3, further including an image data recording means for recording said endoscope image signals received from said plurality of said endoscope devices.

5. An endoscope image data filing system as defined in claim 4, said image data recording means records said endoscope image signals in analog form.

6. An endoscope image data filing system as defined in claim 4, further includes a control means for controlling said first recording means, said second recording means, and said image data recording means.

7. An endoscope image data filing system as defined in any of claims 1, 2 and 3, further includes:
   a management information input means for inputting management information, said management information being used for management of said endoscope image signals received from said plurality of said endoscope devices; and
   a control means for producing a database on the basis of said management information, and for further controlling said first recording means and said second recording means, in accordance with at least said database.

8. An endoscope image data filing system as defined in claim 7, wherein said management information comprises a plurality of management codes.

9. An endoscope image data filing system as defined in any of claims 1, 2, 3, 4, 7 and 8, further including one or more reproducing means for reproducing said compressed image information recorded by said first recording means or by said second recording means.

10. An endoscope image data managing method, comprising:
    an image signal producing step for obtaining images of the inside of a coelom by means of a plurality of endoscope devices, and for further producing endoscope image signals with respect to said obtained images;
    a compression step for compressing said endoscope image signals received from said plurality of said endoscope devices by using at least one reversible compression method for reversibly compressing said endoscope image signals and at least one irreversible compression method for irreversibly compressing said endoscope image signals;
    a first recording step for recording compressed image information produced in said compression step by both said reversible compression method and said irreversible compression method; and a second recording step for re-recording compressed image information recorded in said first recording step, said compressed image information produced by using said irreversible compression method in said compression step.

11. An endoscope image data managing method as defined in claim 10, further including an image data recording step for recording said endoscope image signals received from said plurality of said endoscope devices.

12. An endoscope image data managing method as defined in claim 10, further including:

a management information input step for inputting management information, said management information being used for management of said endoscope image signals received from said plurality of said endoscope devices; and a database producing step for producing a database on the basis of said management information, said database being used for control of said first recording step and of said second recording step.

13. An endoscope image data managing method as defined in any of claims 10, 11 and 12, further including a reproducing step for reproducing said compressed image information recorded in said first recording step or in said second recording step.

* * * * *